United States Patent [19]
Gilbert et al.

[11] Patent Number: 5,098,899
[45] Date of Patent: Mar. 24, 1992

[54] METHOD FOR THERAPEUTICALLY TREATING PSORIATIC ARTHRITIS USING VITAMIN D ANALOGUES AND METABOLITES

[75] Inventors: Lawrence Gilbert, Hingham; Michael F. Holick, Sudbury, both of Mass.

[73] Assignee: Trustees of Boston University, Boston, Mass.

[21] Appl. No.: 627,901

[22] Filed: Dec. 14, 1990

Related U.S. Application Data

[63] Continuation of Ser. No. 320,028, Mar. 6, 1989, abandoned.

[51] Int. Cl.$^5$ ............... A01N 45/00; A61K 31/59
[52] U.S. Cl. ................................. 514/167; 514/168; 514/35; 514/863
[58] Field of Search ............ 514/167, 168, 863, 35

[56] References Cited

U.S. PATENT DOCUMENTS

| | | | |
|---|---|---|---|
| 3,903,071 | 9/1975 | Holmes | 424/284 |
| 4,325,965 | 4/1982 | Chiba | 424/284 |
| 4,326,055 | 4/1982 | Loeliger | 514/863 |
| 4,410,515 | 10/1983 | Holick et al. | 424/180 |
| 4,521,410 | 6/1985 | Holick et al. | 514/26 |
| 4,610,978 | 9/1986 | Dikstein et al. | 514/46 |
| 4,728,643 | 3/1988 | Holick et al. | 514/167 |
| 4,804,651 | 2/1989 | Duvic et al. | 514/50 |

FOREIGN PATENT DOCUMENTS

| | | |
|---|---|---|
| 0129003 | 12/1984 | European Pat. Off. . |
| 0177920 | 10/1985 | European Pat. Off. . |

OTHER PUBLICATIONS

Robert N. Bennet, "Psoriatic Arthritis", in *Arthritis and Allied Conditions: A Textbook of Rheumatology*, (by Daniel J. McCarthy), 11th edition, Lea & Febiger, 1989, Chapter 61, pp. 954–971.

*Primary Examiner*—Asok Pal
*Attorney, Agent, or Firm*—David Prashker

[57] ABSTRACT

A novel and effective treatment of psoriatic arthritis is provided using biologically active forms of vitamin D analogues and metabolites, and preferably 1,25-dihydroxy vitamin $D_3$. The administration of vitamin D analogues and metabolites may be made orally, topically, or parenterally. Substitive improvements in both the arthritic condition and skin lesions result after approximately two month's treatment when effective dosages are provided and maintained.

7 Claims, No Drawings

METHOD FOR THERAPEUTICALLY TREATING PSORIATIC ARTHRITIS USING VITAMIN D ANALOGUES AND METABOLITES

This application is a continuation of application Ser. No. 320,028, filed Mar. 6, 1989, now abandoned.

FIELD OF THE INVENTION

The present invention is concerned with specific disease states and pathological disorders, and is particularly directed to therapeutically treating psoriatic arthritis as a singular disease and pathological state.

BACKGROUND OF THE INVENTION

Although psoriatic arthritis is today recognized and as a distinct disease and pathological state based on its natural evolution, prognosis, and response to available modes of treatment, its consideration and present status as a distinct and separate clinical entity separate from either psoriasis and/or rheumatoid arthritis required both time and in-depth medical knowledge. In retrospect, the first detailed description of psoriatic arthritis appeared in the doctoral thesis of Charles Bourdillion [*Psoriasis et Arthropathies*, These de Paris, Volume 298, 1988]; and in several mid-19th century case reports of a unique relationship between psoriasis and arthritis published by 1904 [Menzen, J., *Arch. Dermatol. Syph.* 70:239-240 (1904)]. For about 30 years thereafter, the idea of psoriatic arthritis being an individual and discrete entity, as opposed to the coincidental occurrence of rheumatoid arthritis and psoriasis, was not generally accepted. Consequently, it was not until the demonstration of rheumatoid factor (RF) in the serum of most patients with typical rheumatoid arthritis in 1948 that the distinction became firmly established. The demonstration and meaning of rheumatoid factor (RF) divided inflammatory arthritis into seropositive and seronegative groupings. Consequently, the realization that the majority of patients with coincident psoriasis and arthritis were in fact seronegative, coupled with the introduction of specific and reliable criteria for the diagnosis of rheumatoid arthritis itself, then firmly established psoriatic arthritis as a separate and distinct disease entity [Rose et al., *Proc. Soc. Exp. Biol. Med.* 68:1-6 (1948); Ragan, C., Arthritis And Allied Conditions, (J.L. Hollander and D.J. McCarthy, editors) 8th Edition, Lee & Febiger, Philadelphia, 1972; Ropes et al., *Bull. Rheum. Dis.* 7:121-124 (1956); and Ropes et al., *Bull. Rheum. Dis.* 9:175-176 (1959)].

Today, rheumatologists have generally accepted the concept of distinctive clinical and radiological features for psoriatic arthritis; and employ them to identify subjects suffering from psoriasis alone and to distinguish those persons suffering from either seronegative or seropositive rheumatoid arthritis without psoriasis. A series of clinical characteristics suggestive of psoriatic arthritis have been developed and verified. Similarly, a detailed description and evaluation of the pathology, etiology, clinical features, patterns of disease onset and distribution, laboratory tests, and radiographic findings of psoriatic arthritic have been extensively investigated and documented. A comprehensive and well documented description of these diagnostic, clinical, and pathological developments and findings identifying psoriatic arthritis as a distinctive disease state and entity is provided by Robert N. Bennett in Arthritis And Allied Conditions, *A Textbook Of Rheumatology*, (Daniel J. McCarthy, Editor) Lee & Febiger, 11th Edition, 1989, pages 954-971, the text of which is expressly incorporated by reference herein.

Psoriatic arthritis can afflict humans with varying degrees of suffering and debilitation. Most patients with psoriatic arthritis have mild disease states affecting only a few joints and follow a rather episodic course. The range of symptoms and duration of disease may extend to forms considered mild, or acute, or even severe in the extreme cases. Many cases of mild disease are well controlled using aspirin or non-salicylic acid substitutes available without prescription as anti-inflammatory agents. In patients with only a few involved joints, corticosteroids injected locally, both into joints and into tendon sheaths have been effective. In the small number of patients (about 5%) developing severe, destructive inflammation that leads to marked disability, a number of different therapeutic approaches have been attempted. Photochemotherapy using oral 8-methoxypsoralenes, followed 2 hours later by photosensitization using ultraviolet light type A (PUVA) has been occasionally successful [Perlman et al., *Ann. Intern. Med.* 91:717-722 (1979)]. Similarly, high dose methotrexate administered parenterally [Black et al., *JAMA* 189:743-747 (1964)] has proven useful. More recent approaches and therapeutic compositions have included: chiral ester compounds of naproxen and naproxol [British Publication No. 2,204,868 printed Nov. 23, 1988]; the inhibiting of interleukin-1 production by monocytes [U.S. Pat. No. 4,778,806]; new substituted phenol compositions useful as anti-inflammatory and anti-arthritic compositions [U.S. Pat. No. 4,708,966]; a polyvalent non-specific immunostimulating vaccine comprising purified protein derivatives from rabies and snake venom [U.S. Pat. No. 4,657,761]; the treating of adrenal glands and affected joints daily with decimetre band electromagnetic fields [Soviet Union Patent No. 1,210,847 printed Feb. 15, 1986]; 6-alkoxy-2-naphthohydroxamic acid compounds useful as lipoxygenase inhibitors [U.S. Pat. No. 4,605,669]; 3-dimetblycarbamoylthyazolo-(4,5-a)-pyridine derivatives [British Patent No. 2,151,623]; pyrazolo-pyridine 3-carboxylic acid derivatives [British Patent No. 2,153,818]; immunosuppressive agents including tetrahydro-1,3-thiazine-4-one compounds [U.S. Pat. No. 4,352,929]; 2(4-(4-chlorophenyl)-benzelyoxy)-2-phenyl-acetic acid derivatives [U.S. Pat. Nos. 4,304,788 and 4,310,544]; and omega-hydroxy-carbonyl-alkyl substituted-dithio-carbanilates active as immunosuppressive agents [U.S. Pat. No. 4,166,866].

The mode and manner of developments and therapeutic treatments for effectively treating psoriatic arthritis thus is markedly different from the comparably intense investigations for effectively treating hyperproliferative skin disorders such as psoriasis itself. Exemplifying the degree of difference and approach has been the therapeutic development of using biologically active vitamin D analogues and metabolites as therapeutic agents.

The initial breakthrough in this field was the demonstration that topical application of radiolabelled 1,25-dihydroxy-7-dehydrocholesterol followed by phototherapy resulted in the detection of tritiated 1,25-dihydroxy vitamin $D_3$ in the circulation. The topical application of such vitamin D analogues has been suggested as an effective method of therapy for diseases involving calcium, phosphorous, and bone metabolism problems [Holick et al., *New England Journal Of Medicine*

303:349-354 (1980); U.S. Pat. No. 4,230,701 and 4,335,210]. Subsequently, a specific biological function for 1,25-dihydroxy-vitamin $D_3$ intracutaneously was demonstrated [Clemens et al., *J. Clin. Endocrinol. Metab.* 56:824-830 (1983); Morimoto et al., *Arch. Dermatol.* 125:231-234 (1989)]. In addition, it has been shown that the topical application of 1-hydroxycholecalciferol, 1,25-hydroxychole-calciferol, 24,25-dihydroxycholecalciferol, and other derivative forms individually are directly effective agents in the skin of persons afflicted with contact dermatitis [European Patent Publication No. 0129003; see also *Vitamin D Molecular, Cellular, And Clinical Endocrinology*, Walter deGruyter & Company, Berlin, Germany, 1988, pp 300-319].

The most recent developments and therapeutic uses for vitamin D analogues and metabolites have been extended to include a variety of other clinical conditions including osteoporosis, rickets, rheumatism, and anti-proliferative agents effective against tumors. Representative of the variety and degree of these vitamin D developments are the following printed publications: European Patent Publication Nos. 250,755 (880107); 1184112 (860611); 205028 (861217); 85112679 (851007); and 87115258 (871019); Japanese publication No. 62004262 (870110); U.S. Pat. Nos. 4,341,774; 4,610,978; 4,613,594; 4,728,643.

It is abundantly clear, therefore, to clinical practitioners and research investigators in the art, that because of the major clinical and pathological distinctions and characteristics which identify and separate psoriatic arthritis from the related pathologies of psoriasis and rheumatoid arthritis individually, there has accordingly been no reason or expectation that the developments and uses of vitamin D analogues and metabolites might have any value or effectiveness on the clinical condition recognized distinctively as psoriatic arthritis. For this reason, and, because effective therapeutic treatments and compositions for psoriatic arthritis continue to be needed especially for those patients suffering from severe, debilitating forms, the possibility of applying vitamin D therapeutic treatments and compositions as therapies for psoriatic arthritis, stands as both unforeseen and unexpected developments and achievements of merit.

SUMMARY OF THE INVENTION

The present invention is a therapeutic method for treating psoriatic arthritis comprising the steps of:

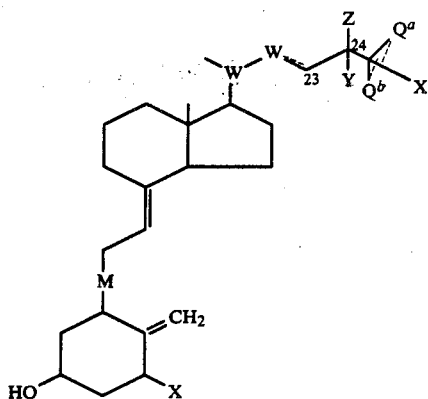

wherein the bond between carbon atoms C-22 and C-23 is a single or double covalent bond;

Y is H, F, $CH_3$, or $CH_2CH_3$;

Z is F, H, or OH;

$Q^a$ is $CF_3$, $CH_3$, $CH_2$, $CH_2OH$, H, or OH;

$Q^b$ is $CF_3$, $CH_2$, or $CH_3$;

X is H, F, or OH;

W is $CH_2$, CH, or O;

M is a double bond or an epoxy group; and administering an effective amount of the compound to the subject.

DETAILED DESCRIPTION OF THE PREFERRED EMBODIMENTS

The present invention is a therapeutic method for oral, topical, and/or parenteral treatment of psoriatic arthritis using vitamin $D_2$, vitamin $D_3$, and biologically active analogues and metabolites of vitamin D. This therapeutic method utilizes active compositions of specified chemical formula which are administered in effective quantities to the afflicted subject for beneficial treatment. While the methodology is empirically demonstrated hereinafter to be especially effective in the treatment of acute or chronic psoriasis arthritis) it is intended for general use in therapeutically treating all degrees of this disease and pathological state. The present invention allows the user to employ quantities of biologically active vitamin D analogues and metabolites in concentrations up to 1,000.0 microgram (hereinafter "ug") preferably, but not exclusively, in a single dose before the subject retires at night to sleep. The timing of the therapeutical regimen for the afflicted subject is not critical.

Conventional knowledge and expectations in this art recognize that application of biologically active vitamin D analogues and metabolites to the subject may cause a substantial increase of calcium uptake in the blood of the subject and/or the release of increased quantities of calcium into the urine. Such side effects are directly attributable to the presence of ingested calcium-containing food (solid or liquid) in the digestive system of the subject at the time the therapeutic dose of biologically active vitamin D analogue or metabolite is administered. One mode of controlling such hypercalcemia and hypercalciuria is by administration of the vitamin D analogue or metabolite at a time when little or no calcium-containing food lies within the digestive system—that is, by fasting, by careful food discrimination, or by administration immediately before sleeping.

The biologically active vitamin D analogues and metabolites useful as therapeutic agents in the present invention are those embodying Formula I or Formula II below.

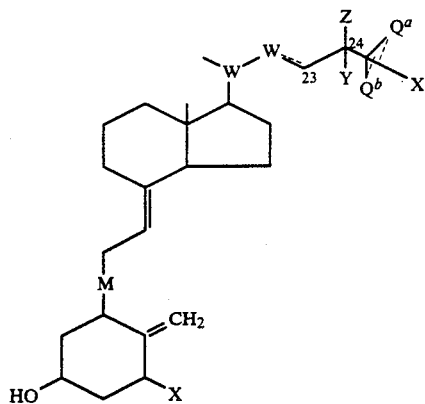

wherein the bond between carbons C-22 and C-23 is single or double;

Y is hydrogen, F, $CH_3$, or $CH_2CH_3$;

Z is F, H, or OH;

$Q^a$ is $CF_3$, $CH_3$, $CH_2$, $CH_2OH$, OH, or hydrogen;

$Q^b$ is $CF_3$, $CH_2$, or $CH_3$;

M is a double bond or an epoxy

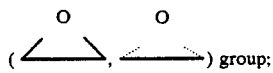
group;

X is H, F, or —OH; and

W is $CH_2$, CH, or O.

When the compounds for Formula I have a double bond at position C-22, they are derivative of vitamin $D_2$; whereas if the bond at that position is single, and there is no alkyl group at C-24, they are derivatives of vitamin $D_3$.

Preferred embodiments of Formula I are those compounds derived from vitamins $D_3$ or $D_2$; 1-hydroxy-vitamins $D_3$ or $D_2$; 1,25-dihydroxy vitamins $D_3$ and $D_b$ 2; 24,25-dihydroxy vitamins $D_3$ or $D_2$; 25,26-dihydroxy vitamins $D_3$ or $D_2$; 1,24,25-trihydroxy vitamins $D_3$ and $D_2$. Most preferred among these are 1-hydroxy-vitamins $D_3$ or $D_2$; 1,24-dihydroxy vitamin $D_2$ or $D_3$; 24,24-difluoro,1,25-dihydroxy vitamin $D_3$; 26,27-hexafluoro,1,25-dihydroxy vitamin $D_3$; and 1,25-dihydroxy vitamins $D_3$ or $D_2$ and the side chain fluoro derivatives of 1,25 $(OH)_2$ vitamin D and 1 (OH) vitamin D.

The synthesis and purification of compositions embodying Formula I are known and conventional in this art. The epoxy derivatives of vitamin $D_3$ are obtained as described in Jpn. Kokai Tokkyo Koho JP 58,216,178 [83,216,178], Dec. 15, 1983. Other derivatives are described in *Vitamin D Molecular, Cellular, And Clinical Endocrinology*, Walter deGruyter & Company, 1988, pp 300–319.

The fluoro derivatives are made or obtained as described in Shiina et al., *Arch. Biochm. Biophy.* 220:90 (1983).

Formula II is:

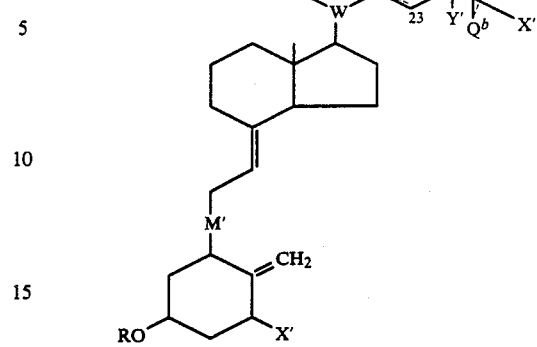

wherein Y' is hydrogen, fluorine, methyl, or ethyl;

Z' is F, H, or X';

$Q^a$, $Q^b$, and W have the same meanings as in Formula I;

M' is a double bond or an epoxy group;

X" is hydrogen, fluorine, or OR;

R is hydrogen, a straight or branched chain glycosidic residue containing 1–20 glycosidic units per residue, or is an orthoester glycoside moiety.

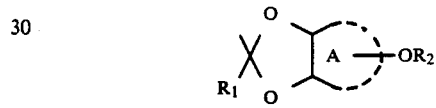

where

A represents a glucofuranosyl or glucopyranosyl ring;

$R_1$ is hydrogen or an alkyl, aralkyl, or aryl group and $R_2$ is hydrogen or a straight or branched chain glycosidic residue containing 1–20 glycosidic units per residue, with the proviso that at least one R entity is either a glycosidic residue or an orthoester glycoside moiety.

Such compounds are water soluble derivatives of Formula I obtained by attaching thereto glycosidic residues preferably by the reactions disclosed in Holick, U.S. Pat. No. 4,410,515. Alternative methods of solubilization comprise conjugating compounds for Formula I to glycosyl orthoester residues as disclosed in U.S. Ser. No. 607,117 by Holick et al., filed May 3, 1984. The disclosures of the aforementioned issued patent and patent application are expressly incorporated by reference herein.

Compounds embodying Formulas I and II respectively of the invention can be administered in any appropriate carrier for oral, topical, or parenteral administration. They can be introduced by any means that effects conditions of psoriatic arthritis in humans. The dosage administered will vary and be dependent upon the age, health, and weight of the recipient; the kind of concurrent treatment, if any; the frequency of treatment; and the nature of the therapeutic effect desired. Generally, daily oral dosage at bedtime of active compounds will be from about 0.001 micrograms/kg to 100 micrograms/kg. Normally, from 0.5 to 50.0 micrograms per day, in one or more oral administrations per day, is effective to yield the desired results.

If the vitamin D analogues and metabolites for Formulas I and II are to be applied topically, they can be admixed in a concentration from about 0.001 to 1,000.0 ug per gram of a pharmacologically inert topical carrier such as a gel, an ointment, a lotion, or a cream; and include such carriers as water, glycerrol, alcohol, propylene glycol, fatty alcohols, triglycerides, fatty acid esters, or mineral oils. Other possible topical carriers are liquid petrolatum, isopropylpalmitate, polyethylene glycol ethanol 95%, polyoxyethylene monolaurate 5% in water, sodium lauryl sulfate 5% in water, and the like. Materials such as anti-oxidants, bumectants, viscosity stabilizers, and the like may be added, if necessary. Also, the active vitamin D composition may be disposed within devices placed on, in, or under the skin; such devices include patches and implants which release the active material into the skin or body either by diffusion or by an active release mechanism.

Similarly, if the vitamin D analogues and metabolites of Formulas I and II are to be given parenterally, they will be prepared in sterile form; in multiple or single dose formats; and dispersed in a fluid carrier such as sterile physiological saline or 5% dextrose solutions commonly used with injectables. In addition, other methods of administration such as transdermal applications can be advantageously employed as well.

The unique and unexpected benefits of therapeutically administering biologically active vitamin D analogues and metabolites conforming to either of Formulas I or II respectively is demonstrated by the individual case histories of the human patients identified hereinafter.

Case History 1

As part of a study being conducted at the Boston University Clinical Research Center at the School of Medicine for the experimental treatment of psoriasis, a 56 year old male patient was treated in an open, uncontrolled trial—initially for psoriasis over a period of 1 calendar year. Prior to beginning the trial treatment at the Center, the subject (over a three month period of time) discontinued medications of any and every kind previously used to treat his affliction except for orally taking a multi-vitamin supplement once a day. Recognizing that the trial treatment was intended initially for treating psoriasis alone, the subject's skin lesions were treated topically with 1,25-dihydroxy vitamin $D_3$ and the treatments monitored individually over a two week time period. The topical administration was made using a petroleum based composition and employed an initial dosage of 3.0 micrograms of 1,25-dihydroxy vitamin $D_3$ per total weight of 1.0 grams of petroleum base, each administration to be made over a two week duration. Concurrently, 0.5 micrograms of 1,25-dihydroxy vitamin $D_3$ was taken orally by the subject once a day before bedtime. The oral dosage was increased incrementally over a four month time by individual increases of 0.25 micrograms every two weeks until the maximum dose of 2.0 micrograms of activated vitamin $D_3$ was orally taken each night. After the sixth month of treatment, the topical dose administered was also increased from 3.0 micrograms to 15.0 micrograms per gram of petrolatum.

By the end of the fourth month of the trials, the subject experienced and observed an unexpected and beneficial side-effect. In addition to being afflicted with psoriasis, the subject male had been previously diagnosed as having arthritis, a condition present since the age of 25. The arthritic condition was present in the ankles, feet, toes, knees, elbows, hands, and left shoulder of the subject. In particular, the left shoulder condition was quite severe and prevented the subject from raising his arm above shoulder length. The unexpected and beneficial side-effects of this therapy were noticed by the subject at the end of the fourth month of treatment during which the subject found he had complete mobility of the left shoulder without any accompanying pain as a result of the oral administration. By the fifth month of treatment, the subject found he was able to freely exercise. Such exercise included walking approximately 1.5 miles daily within about 25 minutes time; and being able to bicycle about 3 miles within 17–18 minutes every other day. By the end of the sixth month of treatment, all other arthritic areas in the body were markedly and substantially improved with major reductions in pain and increased joint mobility; this improvement was so enhanced that at the end of the seventh month of treatment, the subject was able to wear normal, penny-loafer style shoes and walked without discomfort for the first time in over 20 years. At the end of the full calendar year of treatment, the subject had significant clearing of skin lesions as the result of topical application. Some treated areas had completely healed with no visible trace and no subsequent occurrence of lesions; other skin areas were completely cleared but required periodic additional topical treatment to remain lesion free. A very few skin areas, most notably on the toes, were cleared of lesions but had resisted complete healing even at the maximum dosage levels then being topically administered.

The subject male also had been routinely monitored on a monthly basis using a Chem 20 profile and a urine test for presence of calcium. Over the one year trial period, the calcium levels remained within normal limits.

Case History 2

Subsequent to the individual subject trial study, the Arthritis Center at the Boston University School of Medicine conducted an open, uncontrolled trial of 5 patients with active psoriatic arthritis using orally administered 1,25-dihydroxy vitamin $D_3$ to determine if this had any beneficial effect on their condition; and, if so, to determine if there was a corresponding improvement in their skin lesions as well. The treatment of these 5 patients was conducted over a period of 3 calendar months and the subjects comprised both males and females with documented individual histories of psoriatic arthritis ranging from less than 1 year to over 25 years of affliction. Each patient was evaluated and individually traced, before treatment to establish a pre-treatment baseline of personal condition. Subsequently, each began a therapeutic regimen beginning with 0.5 micrograms of activated vitamin $D_3$ which was incrementally increased every two weeks until a maximum dosage of 2.0 micrograms was taken orally once a day.

At the end of three calendar months of vitamin $D_3$ therapy, one patient found no meaningful improvement and withdrew from the study because of ineffectiveness and an inability to achieve a maximum therapeutic dose secondary to hypercalciuria. Of the remaining 4 patients, each was able to achieve the maximum dosage of 2.0 micrograms taken orally, and 2 of 3 showed a marked improvement in their arthritic condition manifested by a decrease in tender joint count of greater than 80% improvement. Each person also showed improvements in skin lesions but the degree of skin lesion improvement was not correlatable with the degree of arthritic improvement as such. The 2 subjects for whom the activate vitamin D3 therapy was effective have continued using the orally administered 1,25-dihydroxy vitamin D3 therapeutic mode of treatment long term and achieved substantial improvement at the continuing dosage level of 2.0 micrograms taken orally once a day.

Case History 3

A male subject aged 35 years with a history of psoriatic arthritis in both elbows for over ten years, was treated topically with 1.0 micrograms of 1,25-dihydroxy vitamin D3 dispersed in 10 grams of petroleum base. After two months of topical treatment, the male patient observed and experienced significant improvement in both his skin lesions and his arthritis.

These case histories individually and cumulatively empirically demonstrate and document the ability of activated vitamin D analogues and metabolites to be therapeutically effective in the treatment of psoriatic arthritis. The case histories demonstrate effective improvement and therapeutic results when the mode of treatment is oral or topical, or oral and topical treatment concurrently. However, it is expected and deemed that the best and most effective mode of treatment is by oral administration of the activated vitamin D analogue and metabolite in an amount of at least 0.5 micrograms taken once as a single dose on a daily basis; however, because of the oral administration preferred route, it is most desirable to reduce the side-effects of calcium build-up (hypercalcemia and hypercalciuria) by administering the active vitamin D compositions immediately prior to bed time in the evening.

The present invention is not to be restricted in form nor limited in scope except by the claims appended hereto.

What we claim is:

1. A therapeutic method for treating psoriatic arthritis in an afflicted living subject as a distinct pathological entity different and distinguishable from the pathologies of psoriasis and rheumatoid arthritis, said psoriatic arthritis treatment method comprising the steps of:

obtaining an anti-psoriatic arthritis compound having the formula

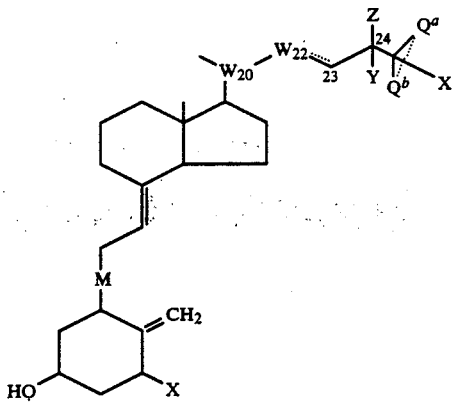

wherein the bond between positions 22 and 23 is a single or double bond;
Y is H, F, $CH_3$, or $CH_2CH_3$;
Z is F, H, or OH;
$Q^a$ is $CF_3$, $CH_3$, $CH_2$, $CH_2OH$, H, or OH;
$Q^b$ is $CF_3$, $CH_2$, or $CH_3$;
X is H, F, or OH;
$W_{22}$ is $CH_2$, CH, or O;
$W_{20}$ is CH;
M is a double bond or an epoxy group; and
administering an effective amount of said anti-psoriatic arthritis compound to the afflicted living subject.

2. A therapeutic method for treating psoriatic arthritis is an afflicted living subject as a distinct pathological entity different and distinguishable from the pathologies of psoriasis and rheumatoid arthritis, said psoriatic arthritis treatment method comprising the steps of:

obtaining an anti-psoriatic arthritis compound having the formula

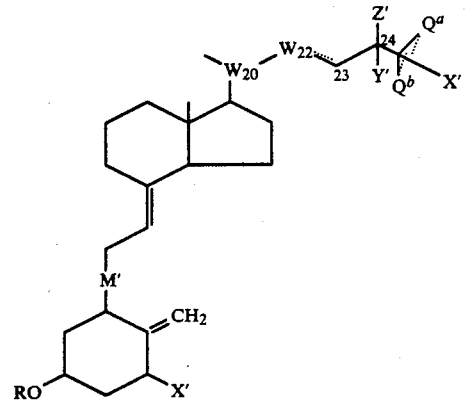

wherein the bond between positions 22 and 23 is a single or double bond;
Y' is H, F, $CH_3$, or $CH_2CH_3$;
Z' is F, H, or X';
$Q^a$ is $CF_3$, $CH_3$, $CH_2$, $CH_2OH$, H, or OH;
$Q^b$ is $CF_3$, $CH_2$, or $CH_3$;
M' is a double bond or an epoxy group;
X' is H, F, or OR;
$W_{22}'$ is $CH_2$, CH, or O;
$W_{20}'$ is CH;
R is hydrogen, straight or branched chain glycosidic residue containg 1-20 glycosidic units per residue, or is an orthoester glycoside moiety having the structure

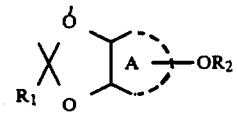

wherein A represents a glucofuranosyl or glucopyranosyl ring;
$R_1$ is hydrogen or an alkyl, aralkyl, or aryl group; and
$R_2$ is hydrogen or a straight or branched chain glycosidic residue containing 1-20 glucosidic units per residue, provided that at least one R entity is a glycosidic residue or an orthoester glycoside moiety; and
administering an effective amount of said anti-psoriatic arthritis compound to the afflicted living subject.

3. The therapeutic method as recited in claim 1 or 2 wherein said compound is one selected from the group consisting of 1-hydroxy vitamin D3; 1-hydroxy vitamin $D_2$; 1.25-dihydroxy vitamin $D_3$, 1,25-dihydroxy vitamin $D_2$; 24,25-dihydroxy vitamin $D_3$, 24,25-dihydroxy vitamin $D_2$; 25,26-dihydroxy vitamin $D_3$; 25,26-dihydroxy vitamin $D_2$; 1,24,25-trihydroxy vitamin $D_3$; 1,24,25-trihydroxy vitamin $D_2$; 1,24-dihydroxy vitamin $D_2$ and $D_3$; 24,24-difluro,1,25-dihydroxy vitamin $D_3$; 26,27-hexafluoro,1,25-dihydroxy vitamin $D_3$; 5,6-epoxy derivatives of vitamin D and its metabolites, and fluoro derivatives of 1-hydroxy vitamin D and of 1,25-dihydroxy vitamin D.

4. The therapeutic method as recited in claim 1 or 2 wherein said compound is administered to the skin of the subject.

5. The therapeutic method as recited in claim 1 or 2 wherein said compound is orally administered to the subject.

6. The therapeutic method as recited in claim 1 or 2 wherein said compound is parenterally administered to the subject.

7. The therapeutic method as recited in claim 1 or 2 wherein said compound is administered to the subject at a concentration ranging from about 0.001–100.0 micrograms per kilogram of body weight.

* * * * *